United States Patent [19]

Park et al.

[11] Patent Number: 5,948,679
[45] Date of Patent: Sep. 7, 1999

[54] HUMAN OVARIAN CARCINOMA CELL LINES

[75] Inventors: Jae-Gahb Park, Seoul National University Hospital, 28, Yongon-dong, Chongno-gu, Seoul, Rep. of Korea, 110-744; Ying Yuan, Seoul, Rep. of Korea; Woo-Ho Kim, Seoul, Rep. of Korea; Hye-Seung Han, Seoul, Rep. of Korea; Jae-Ho Lee, Seoul, Rep. of Korea; Hyun-Sook Park, Seoul, Rep. of Korea; June-Key Chung, Seoul, Rep. of Korea; Soon-Beom Kang, Seoul, Rep. of Korea

[73] Assignee: Jae-Gahb Park, Rep. of Korea

[21] Appl. No.: 09/136,745

[22] Filed: Aug. 19, 1998
[51] Int. Cl.$^6$ ............................................. C12N 5/08
[52] U.S. Cl. ............................................. 435/371; 435/366
[58] Field of Search ................................ 435/366, 371

*Primary Examiner*—Nancy Degen
*Assistant Examiner*—Robert Schwartzman
*Attorney, Agent, or Firm*—Anderson, Kill & Olick

[57] ABSTRACT

A human ovarian carcinoma cell line having an in-frame 3-bp deletion at codons 255 and 256 in exon 7 of the p53 gene, a nonsense mutation of codon 1815 in exon 23 of the BRCA1 gene, and a missense mutation of codon 723 in exon 19 of the hMLH1 gene.

1 Claim, 9 Drawing Sheets

Normal

SNU-251

HUMAN OVARIAN CARCINOMA CELL LINES

FIELD OF THE INVENTION

The present invention relates to human ovarian carcinoma cell lines. More specifically, it pertains to permanent human ovarian carcinoma cell lines cultured from the primary and metastatic tumors of Korean patients, which show various mutations in the tumor suppressor genes p53, BRCA1 and hMLH1.

BACKGROUND OF THE INVENTION

Ovarian carcinoma remains the most lethal gynecologic malignancy. It has been reported to be the fifth most common cancer and the fourth leading cause of cancer mortality among women in the United States(Maller, B. A., et al., *SEER Cancer Statistics Review:* 1973–1990, Bethesda, Md., National Cancer Institute(1993)).

Due to the lack of powerful diagnostic tests and also to the absence of any overt symptoms, early detection of ovarian cancer is difficult. In approximately two-thirds of patients, the disease is at an advanced stage(III or IV) at the time of diagnosis(Boring, C. C., et al., "Cancer Statistics", *Ca. Cancer J. Clin.*, 44, 7–26(1994); Coppleson, M., et al., *Gynecologic Oncology: Fundamental Principles and Clinical Practice,* 2nd ed, London, Churchill Livingstone Press (1992); and Hung, Y. C., et al., "The Female Reproductive System: Cell Lines from Tumor of the Human Ovary and Uterus", in Hay, R. J., et al., *Atlas of Human Tumor Cell Lines,* Academic Press, San Diego, pp 359–386(1994)). Currently, no effective treatment strategies exist, and the long-term prognosis for patients with advanced disease has not improved significantly over the last ten years.

All of these clinical problems are due primarily to a poor understanding of the biological behavior of this tumor. The development of new strategies for diagnosis and treatment must be based on a sound scientific foundation, and in this line, it is very important to have clinically relevant in vitro models to help us study the biology of this malignant disease. The establishment of permanent human ovarian carcinoma cell lines is essential for a multitude of in vitro investigations, while such cultured cancer cell lines can also be used for the production of tumor-associated monoclonal antibodies which can be used for detecting and monitoring the disease(Kabawat, S. E., et al., "Immunopathologic Common Surface Antigens of Human Ovarian Tumors of Serous Endometrioid and Clear Cell Types", *Am. J. Clin. Pathol.,* 79, 98–104(1983)).

Numerous studies on ovarian carcinomas have reported genetic alterations in oncogenes and tumor suppressor genes (Piver, M. S., et al., "Epidemiology and Etiology of Ovarian Cancer, *Semin. Oncol.,* 18, 177–185(1991)). Specifically, amplification or activation of the oncogenes HER-2/neu, K-ras and c-myc, as well as inactivation of the tumor suppressor genes p53, BRCA1 and the human mismatch repair genes hMLH1, hMSH2, hPMS1 and hPMS2, have been detected in ovarian cancers.

Mutation of the p53 gene, often accompanied by overexpression of mutant p53 protein, is the most frequent molecular genetic event described to date in human cancers (Greenblatt, M. S., et al., "Mutations in the p53 Tumor Suppressor Gene: Clues to Cancer Etiology and Molecular Pathogenesis", *Cancer Res.,* 54, 4855–4878(1994)). It has been reported that mutation of the p53 gene occurs in about 30–50% of ovarian cancers(Berchuck, A., et al., "The p53 Tumor Suppressor Gene Frequently Altered in Gynecologic Cancers, *Am. J. Obstet. Gynecol.,* 170, 246–252(1994)).

Well-established and characterized permanent human ovarian carcinoma cell lines can therefore provide useful tools for in vitro studies related to human ovarian carcinomas, but no cell line containing inactivated tumor suppressor gene BRCA1 has been successfully established heretofore.

Accordingly, there exists a need to develop a novel permanent human ovarian carcinoma cell line.

SUMMARY OF THE INVENTION

Accordingly, it is a primary object of the present invention to provide a permanent human ovarian carcinoma cell line.

In accordance with the present invention, there are provided permanent human ovarian carcinoma cell lines cultured from primary and metastatic tumors of Korean patients, which show various mutations in related tumor suppressor genes, i.e., p53, BRCA1 and hMLH1 genes. In particular, the present invention provides a human ovarian carcinoma cell line designated SNU-251 which has an in-frame 3-bp deletion at codons 255 and 256 in exon 7 of the p53 gene, a nonsense mutation of codon 1815 in exon 23 of the BRCA1 gene, and a missense mutation of codon 723 in exon 19 of the hMLH1 gene.

BRIEF DESCRIPTION OF THE DRAWINGS

The above and other objects and features of the present invention will become apparent from the following description of the invention, when taken in conjunction with the accompanying drawings, in which.

DETAILED DESCRIPTION OF THE INVENTION

Figure 1A:
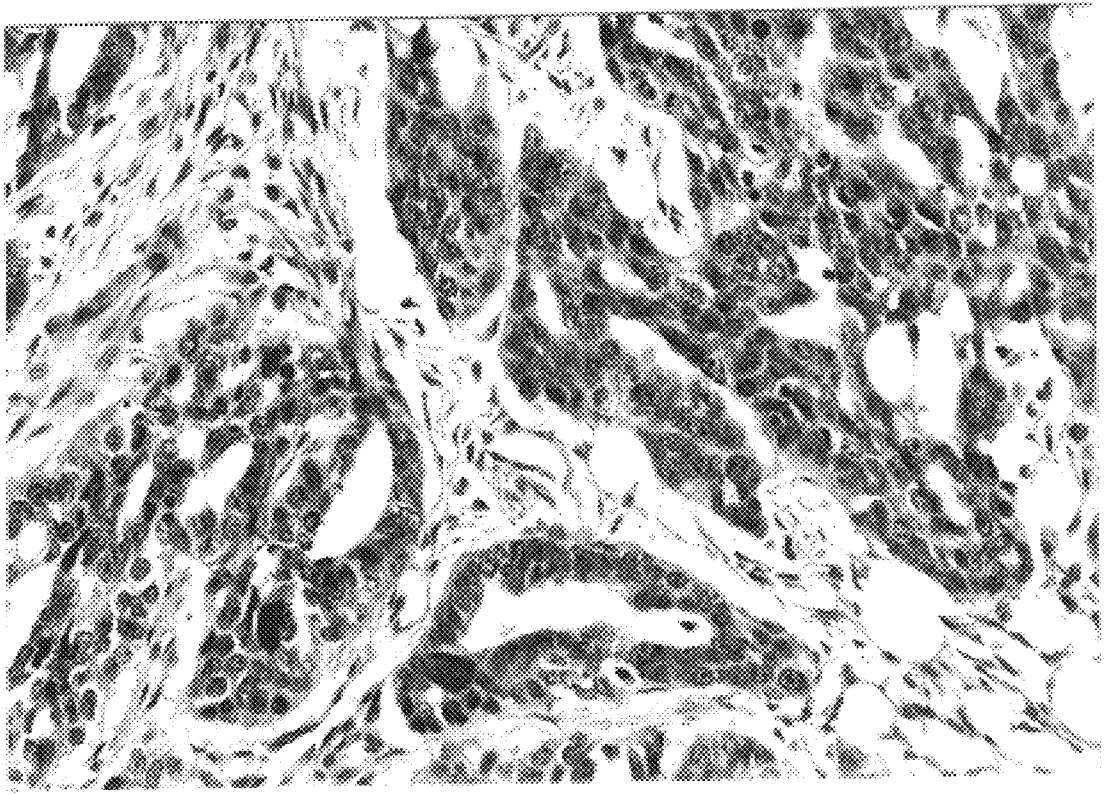
FIG. 1A shows the morphology of the primary tumor of cell line SNU-119 and FIG. 1B, that of cultured cells of SNU-119.

The present invention provides five human ovarian carcinoma cell lines which were cultured from primary and metastatic tumors of Korean patients, and they were designated SNU-8, SNU-119, SNU-251, SNU-563 and SNU-840, respectively.

SNU-8 and SNU-119 are classified as serous adenocarcinomas, the most common pathological type of ovarian cancer from which most of the previously established ovarian carcinoma cell lines have been derived. Further, SNU-251 and SNU-563 are classified as endometrioid carcinomas, and SNU-840, as a malignant Brenner tumor. The endometrioid carcinoma and malignant Brenner tumor are rather rare types of ovarian cancer, accounting for 16–30% and 1% of all ovarian cancers, respectively.

The growth of the above cell lines can be stabilized when cultured for at least 20 passages. The stabilized cell lines show population doubling times in the range of 40 to 67 hours and are all highly viable. All lines are unique as proven by DNA fingerprinting analysis and free of mycoplasma or bacteria contamination. In cell lines SNU-8 and SNU-840, elevated levels of CA125 antigen secretion were detected, whereas CEA is undetectable in all five lines.

Four different mutations in functional and highly conserved regions of the p53 gene exist in three of the five lines (60%), namely in SNU-119, SNU-251 and SNU-563. Included are two missense mutations, one in-frame 3 base-pair deletion and one out-of-frame 1 base-pair deletion.

All four mutations were located in the highly conserved regions from exon 5 to exon 8, which are believed to encode the most functional parts of the p53 molecule, similar to those reported in many other human cancers(Nigro, S. J., et al., Mutations in the p53 Gene Occur in Diverse Human Tumor Types, *Nature,* 342, 705–708(1989)).

Moreover, cell line SNU-251 has a nonsense mutation in the BRCA1 gene. The change of codon 1815(TGG) in exon 23 to a stop codon(TGA) would produce a truncated protein lacking the last 44 amino acids of the C-terminus. No wild-type sequence of the BRCA1 gene can be detected in this cell line, which strongly suggests that the mutation is either homozygous or hemizygous.

The BRCA1 gene is a recently isolated hereditary breast and ovarian cancer susceptibility gene(Miki, Y., et al., A Strong Candidate for the Breast and Ovarian Cancer Susceptibility Gene BRCA1, *Science,* 266, 66–71(1994)). Unlike most other tumor suppressor genes involved in familial cancer syndromes, it has been reported that inherited germline mutations in the BRCA1 gene were found in 50–60% of familial breast and ovarian cancer kindreds (Shattuck-Eidens, D., et al., A Collaborative Survey of 80 Mutations of Germline Mutations in the BRCA1 Breast and Ovarian Cancer Susceptibility Gene, *J. Am. Med. Assoc.,* 273, 535–541(1995); Futreal, P. A., et al., "BRCA1 Mutations in Primary Breast and Ovarian Carcinomas", *Science,* 266, 120–122(1994); and Castilla, L. H., et al., "Mutations in the BRCA1 Gene in Families with Early-Onset Breast and Ovarian Cancer", *Nature Genet.,* 8, 387–391(1994)), while somatic mutations were identified in less than 10% of sporadic ovarian cancers and none of sporadic breast cancers (Merajver, S. D., et al., "Somatic Mutations in the BRCA1 Gene in Sporadic Ovarian Tumors", *Nature Genet.,* 9, 439–443(1995); and Hosking, L., et al., "A Somatic BRCA1 Mutation in an Ovarian Tumor", *Nature Genet.,* 9, 343–344 (1995)). Having lost both of the wild-type alleles of the BRCA1 gene and lacking the capability of normal BRCA1 expression, SNU-251 may serve as an unusual and important in vitro model for studies related to ovarian carcinoma and the BRCA1 gene.

SNU-251 also has an additional heterozygous mutation of the hMLH1 gene, though it is genetically stable in a replication error test. Interestingly, SNU-251 simultaneously contains mutations of three different tumor suppressor genes, p53, BRCA1 and hMLH1. As a consequence, cell line SNU-251 is a uniquely useful model for in-depth studies of ovarian carcinoma. Human ovarian carcinoma cell line SNU-251 was deposited on Nov. 21, 1998 with the Korean Cell Line Research Foundation(KCLRF) (Address: Cancer Research Institute, Seoul National University College of Medicine, 28 Yongon-dong, Chongno-Gu, Seoul, 110-744, Republic of Korea) under the terms of the Budapest Treaty on the International Recognition of the Deposit of Microorganism for the Purpose of Patent Procedure under the accession number of KCLRF-BP-00020.

A test on the CA125 expression/secretion by the five cell lines of the present invention shows that SNU-8 produces a high level of CA125, as does SNU-840 which was derived from a malignant Brenner tumor. The tumor marker CA125, detected by the mouse monoclonal antibody OC-125 established by Bast et al.(Bast, R. C., Jr., et al., Reactivity of a Monoclonal Antibody with Human Ovarian Carcinoma, *J. Clin. Invest.,* 68, 1331–1337(1981); and Bast, R. C., Jr., et al., "A Radioimmunoassay Using a Monoclonal Antibody to Monitor the Course of Epithelial Ovarian Cancer", *New Engl. J. Med.,* 309, 883–887(1983)), is a relatively specific tumor marker for ovarian serous cystadenocarcinoma.

The five ovarian carcinoma cell lines of the present invention constitute a panel of multiple subtypes that should serve as useful tools for further studies on the biology and carcinogenesis of human ovarian carcinoma.

The following Examples and Test Examples are intended to further illustrate the present invention without limiting its scope.

Further, percentages given below for solid in solid mixture, liquid in liquid, and solid in liquid are on a wt/wt, vol/vol and wt/vol basis, respectively, unless specifically indicated otherwise.

EXAMPLE

Establishment of Ovarian Carcinoma Cell Lines

Cell lines were established from the pathologically-proven ovarian carcinomas of five Korean ovarian carcinoma patients whose relevant clinical information is summarized in Table 1.

TABLE 1

Origin of Ovarian Carcinoma Cell Lines

| Cell Line | Date of Initiation | Age | Prior therapy | Primary tumor site | Cultured tumor site | Pathological diagnosis |
|---|---|---|---|---|---|---|
| SNU-8 | Jul/87 | 55 | CAP[a] | Ovary | Ascites | Serous cystadenocarcinoma |
| SNU-119 | Feb/89 | 50 | CAP + 5-FU[b] | Ovary | Ascites | Serous cystadenocarcinoma |
| SNU-251 | Sep/89 | 47 | CAP + EtP[c] | Ovary | Ascites | Endometrioid carcinoma |
| SNU-563 | Jan/91 | 54 | None | Ovary | Primary | Endometrioid carcinoma |
| SNU-840 | Mar/92 | 45 | None | Ovary | Primary | Malignant Brenner tumor |

[a]CAP: cyclophosphamide, adriamycin, cisplatin
[b]5-FU: 5-fluorouracil
[c]EtP: etoposide, cisplatin Specifically, three cell lines were originated from malignant ascites and two from solid tumors. Ascitic fluids from the patients were collected, pelleted, washed with phosphate buffered saline(PBS), and resuspended in a growth medium (i.e., "AR5" medium described below), and cells were seeded into 25-cm² flasks. Solid tumor tissues were finely minced with scissors and dissociated into small aggregates by repeated pipetting. For primary tumor culture, invasive areas were used whenever possible. Tumor cells were initially cultured in ACL-4 medium supplemented with 5% heat-inactivated fetal bovine serum("AR5" medium). ACL-4 is a fully-defined medium formulated for the selective growth of human lung adenocarcinoma, and has proved useful in the establishment of colorectal cancer cell lines (Brower, M., et al., "Growth of Cell Lines and Clinical Specimens of Human Non-small-cell Lung Cancer in a Serum-free Defined Medium", Cancer Res., 46, 798–806 (1986); and Park, J. G., et al., "Characteristics of Cell Lines Established from Human Colorectal Carcinoma", Cancer Res., 47, 6710–6718(1987)). The composition of ACL-4 medium was as follows: RPMI 1640 as a basal medium, insulin(20 mg/ml), transferrin(10 mg/ml), sodium selenite (25 nM), hydrocortisone(50 nM), epidermal growth factor(1 ng/ml), ethanolamine(10 mM), phosphorylethanolamide(10 mM), triiodothyronine (100 pM), bovine serum albumin (2 mg/ml), HEPES buffer(10 mM), glutamine(2 mM) and sodium pyruvate(0.5 mM). RPMI 1640, glutamine and sodium pyruvate were purchased from GIBCO/BRL(Grand Island, N.Y.); epidermal growth factor(EGF) was obtained from Collaborative Research (Waltham, Mass.); and all other reagents were obtained from Sigma(St. Louis, Mo.).

Initial cell passage was performed when heavy tumor cell growth was observed, usually 2 to 4 weeks after initial culture. Subsequent passages were performed every 1 or 2 weeks. Adherent cultures were passaged at sub-confluence after trypsinization. Differential trypsinization was used in the initial cultures with noted stromal-cell growth to obtain a pure tumor-cell population(Park, J. G., et al., supra).

After establishment, cultures were maintained in RPMI 1640 supplemented with 10% heat-inactivated fetal bovine serum("R10" medium). Cell cultures were maintained in humidified incubators at 37° C. in an atmosphere of 5% $CO_2$ and 95% air.

The following Test Examples were performed to exhibit the characteristics of the established ovarian carcinoma cell lines.

Test Example 1

Growth Characteristics

Population doubling times were determined by seeding $3 \times 10^5$ viable cells into 25-cm² flasks and performing daily counts for 14 or more days. Culture media were refreshed every 3 or 4 days and 24 hours prior to counting. For determination of cell viability, a dye-exclusion procedure using the 0.4% Trypan-blue staining method was performed and the number of viable cells was counted under a microscope using a hemocytometer(Freshney, R. I., Culture of animal cells(3rd ed), Wiley-Liss, New York, pp 288–289 (1994)).

The result is shown in Table 2, wherein the population doubling times ranged from 40 to 67 hrs, and the cell viability varied from 81 to 97%.

TABLE 2

Characteristics of Ovarian Carcinoma Cell Lines

| | | Cell line | | | | |
|---|---|---|---|---|---|---|
| | | SNU-8 | SNU-119 | SNU-251 | SNU-563 | SNU-840 |
| Passage | | 33 | 24 | 21 | 20 | 48 |
| Population doubling time(hr) | | 44 | 53 | 46 | 67 | 40 |
| Cell viability(%) | | 89 | 91 | 97 | 81 | 93 |
| CA125 antigen | Cell lysate | +[a] | –[b] | – | – | + |
| | Supernatant | + | – | – | – | + |

[a]+: elevated
[b]–: under detectable level

Test Example 2

In Vitro Morphology

For morphological studies of the cell lines, cells grown in 75-cm² culture flasks were observed daily by phase-contrast microscopy and histopathologically compared with the original tumors. The results are shown in FIGS. 1A, 1B, 2A, 2B, 3A and 3B.

The primary tumors of SNU-8 and SNU-119 were partly solid, cystic and unilocular, and contained yellowish serous fluids with papillary configurations. The case of SNU-8 involved the bilateral mesosalpinx. As shown in FIG. 1A, the microscopic features of the primary tumor of SNU-119 exhibits nuclear atypia, high mitotic activity, stratification, glandular complexity, branching papillary fronds, and stromal invasion. A large number of tumor cells show a solid growth pattern and are more pleomorphic than the tumor cells of a metastatic lesion. The tumor cells also form the complicated glands or solid nests composed of atypical cells with desmoplastic stromal cells.

Figure 2A:
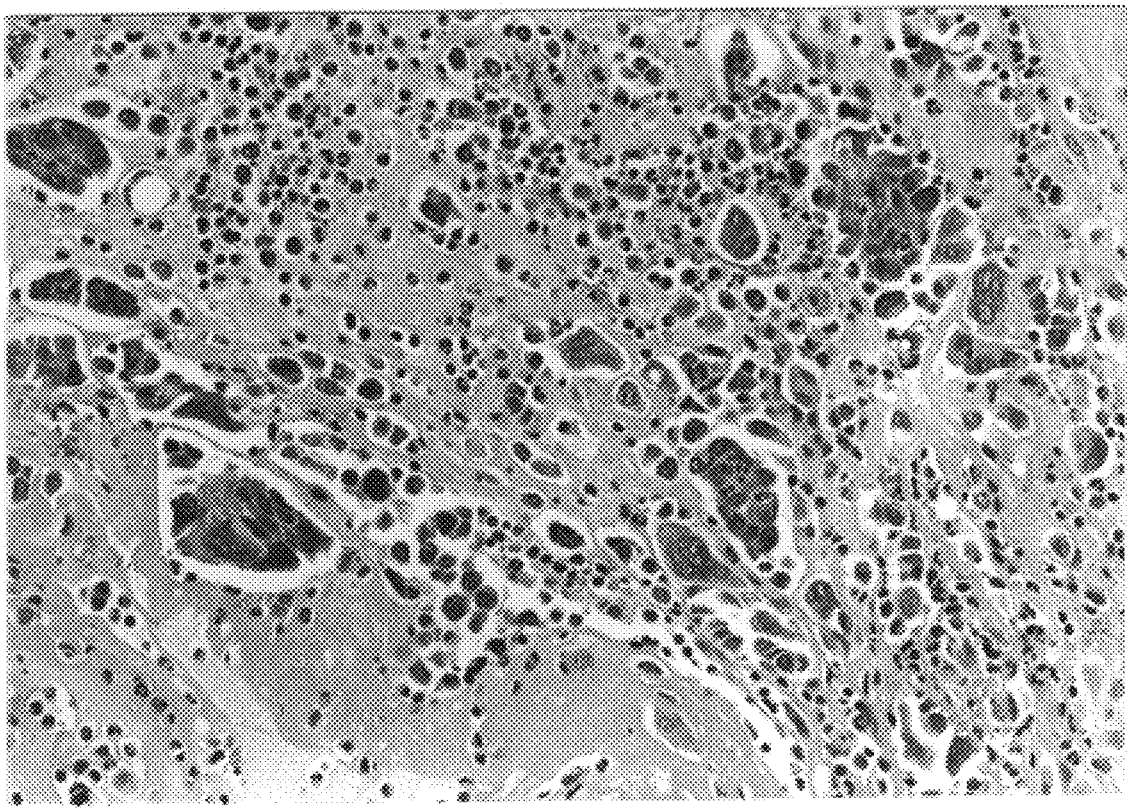
FIG. 2A displays the morphology of the primary tumor of cell line SNU-251 and FIG. 2B, that of cultured cells of SNU-251.

Two endometrioid carcinoma cell lines were derived from malignant ascitic fluids(SNU-251) and primary ovarian tumor (SNU-563). The primary masses showed solid features with focal areas of cystic spaces containing mucoid material and hemorrhagic coagulum. In the case of SNU-563, metastatic nodules were noted in the serosal surface of the uterus and the omentum. As can be seen in FIG. 2A, the tumor cells of SNU-251 are very pleomorphic and atypical. Multinucleated or mononucleated bizarre giant cells are frequently noted in the necrotic background, and show a papillary configuration or single cell pattern. The tumor cells of SNU-563 are very similar in appearance to the ordinary type of endometrial adenocarcinoma accompanied by stromal lymphoplasma cell infiltration. In some areas, though, the tumor glands are small and tubular or solid. The tumor cells in these areas are composed of highly atypical large cells characterized by vesicular nuclei, prominent eosinophilic nucleoli, a plump eosinophilic cytoplasm and numerous typical or atypical mitoses. Multinucleated giant cells are frequently seen.

Figure 3A:
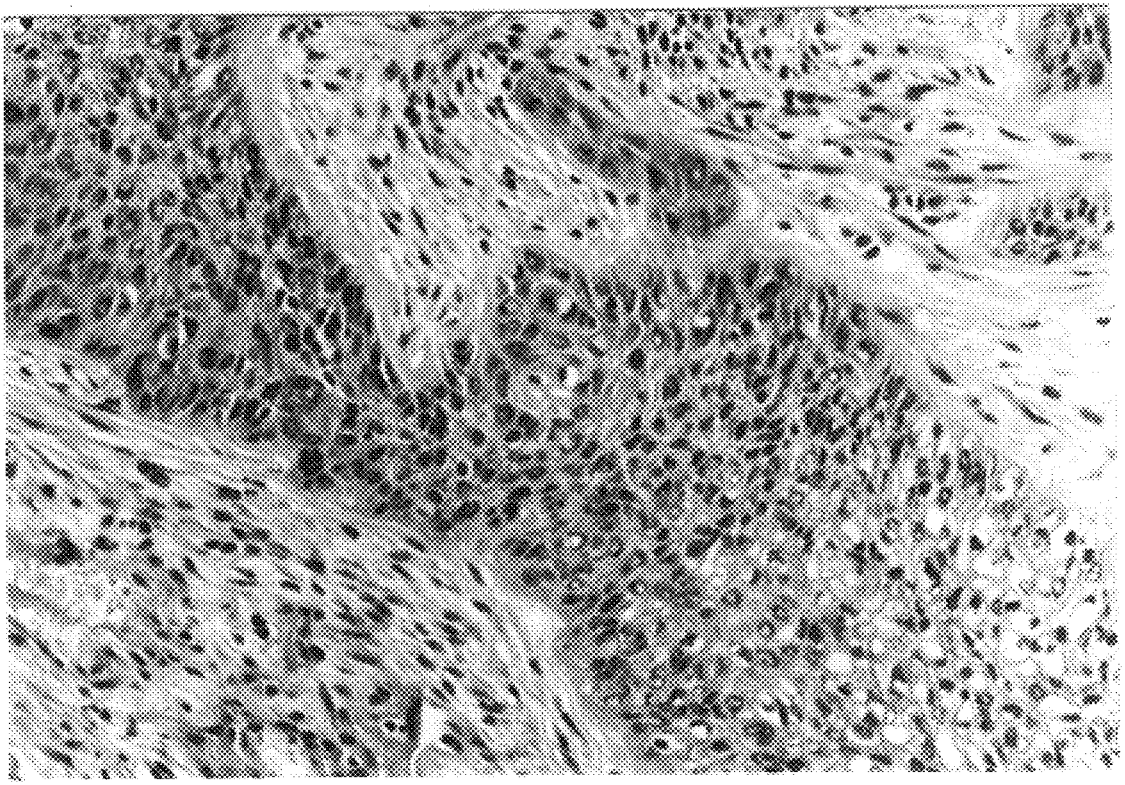
FIG. 3A presents the morphology of the primary tumor of cell line SNU-251 and FIG. 3B, that of cultured cells of SNU-251.

Cell line SNU-840 was established from the primary lesion of a malignant Brenner tumor. Bilateral ovarian masses were diagnosed, with metastasis to the myometrium of the uterus. Grossly, the tumor was firm, yellowish gray, and fibroma-like, with small cystic areas filled with opaque yellowish brown fluid. As can be seen in FIG. 3A, the tumor consists of invading solid and cystic nests of epithelial cells resembling transitional epithelium surrounded by abundant dense fibrotic stroma with inflammatory cell infiltration. Foci which are pseudoglandular and show the features of squamous cell carcinoma are seen. Dystrophic calcification is also noted. The degree of atypia of the tumor cells is equivalent to grade III transitional carcinoma.

Figure 1B:
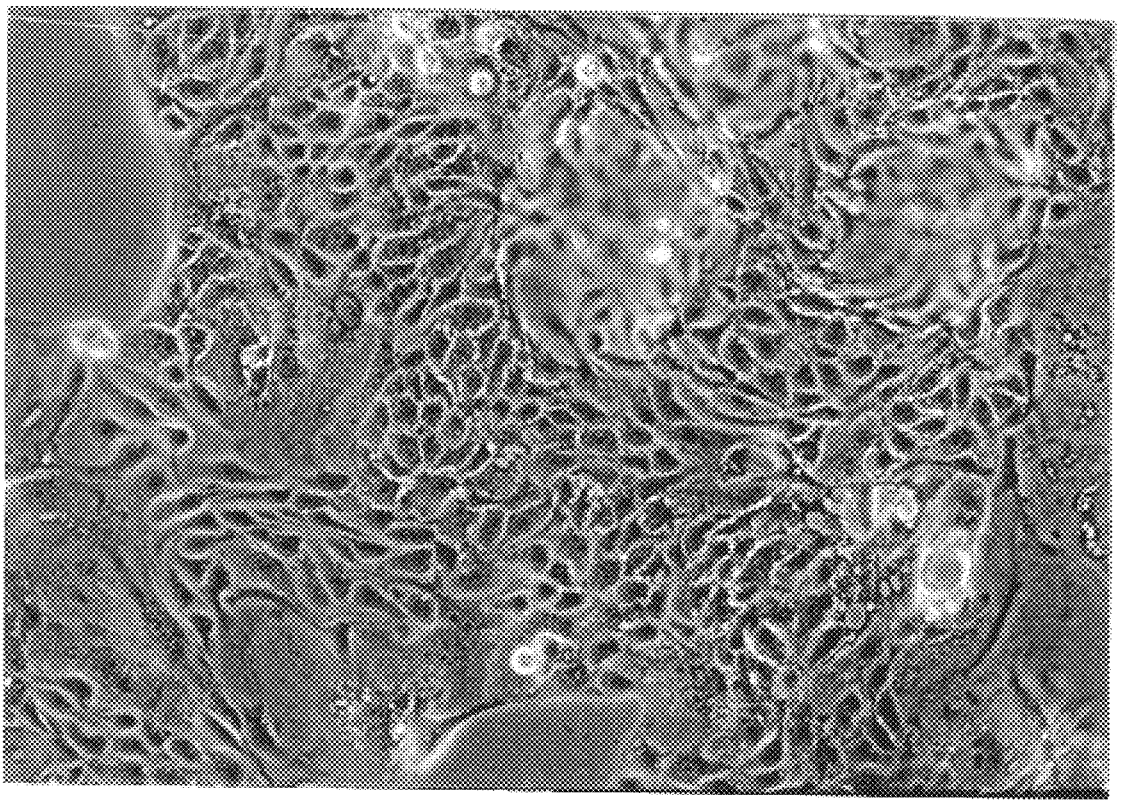
Figure 2B:
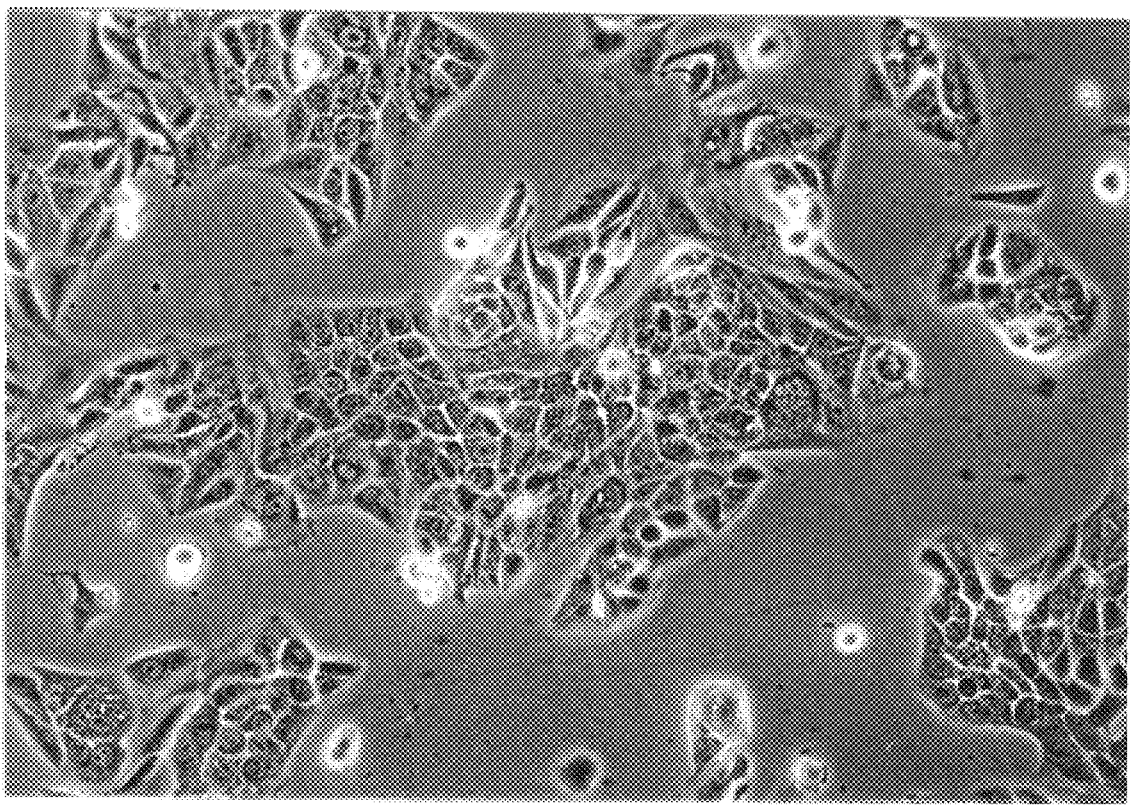
Figure 3B:
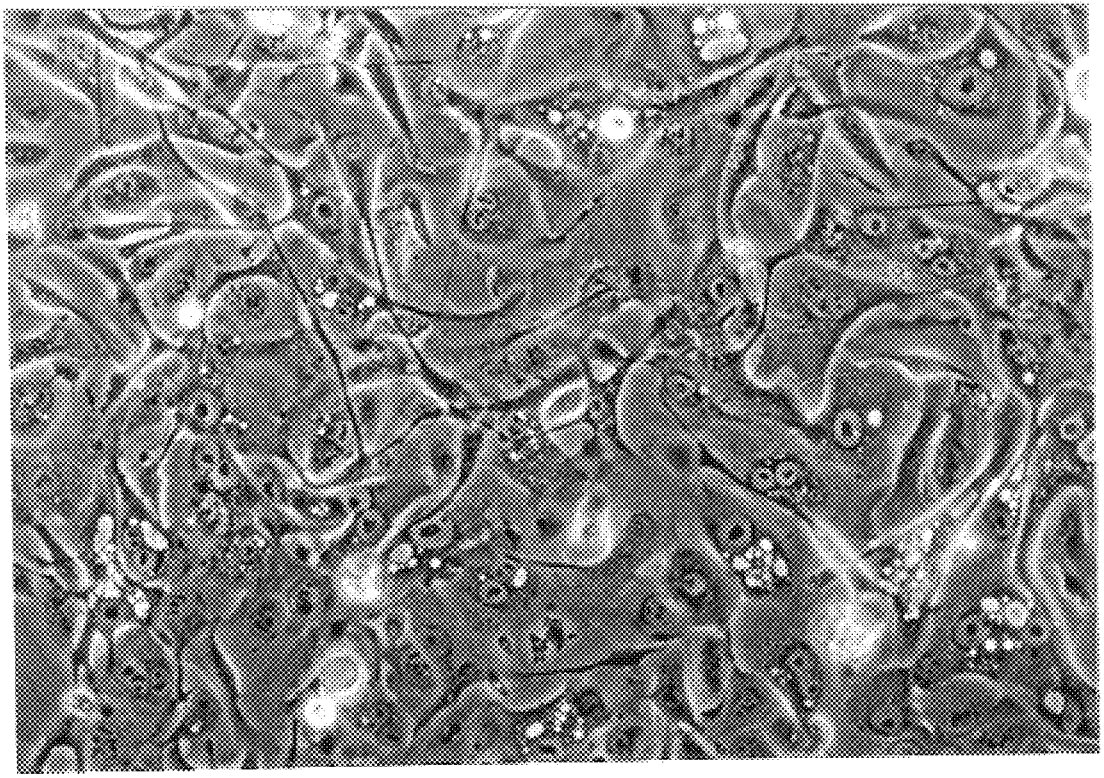

In culture, all the cell lines grew as monolayers of substrate-adherent cells, and showed polygonal morphology with large, round, vesicular nuclei with several nucleoli (FIGS. 1B, 2B and 3B). Cell lines SNU-251 and SNU-563 consist of many multinucleated giant cells, as seen in the primary tumors.

Test Example 3

Mycoplasma Test

A PCR-dependent method was employed to test for contamination by mycoplasma in the cell lines(Goding, J. M., "Detection of Mycoplasma Contamination", in *Monoclonal Antibodies: Principles and Practice*(3rd ed), Academic Press, San Diego, pp 181–183(1996)).

Consequently, all lines were proved to be free from contamination by mycoplasma or bacteria.

Test Example 4

Antigen Expression and Secretion

Protein levels of the tumor-associated antigens CA125 and carcinoembryonic antigen(CEA) in cell lysate and culture supernatant were measured by radioimmunoassay. Cells ($1\times10^6$) were seeded into two 75-cm$^2$ flasks and washed three times with PBS when semiconfluent. Three days later, cells from one flask were counted after trypsinization and then discarded. Cells from the other flask were harvested using a cell scraper, washed three times with PBS, resuspended in 1% Nonidet-P40 with 100 mm phenylmethylsulfonyl fluoride (approximately 5 to 10 ng protein/ml), sonicated twice on ice for 15 seconds, and stored at −70° C. until assayed.

Supernatant fluids from the same flask were collected, clarified, and stored frozen until assayed. CA125 and CEA were measured with immunoradiometric assay kits (Centocor, Pennsylvania, U.S.A.).

As can be seen in Table 2, protein levels of CA125 in two lines, SNU-8 and SNU-840, are significantly elevated both in cultured cell lysate and in supernatant fluids, while in SNU-251, they are slightly elevated; in the other two, no elevation could be detected. For CEA, all protein levels in both cell lysate and supernatant fluids were below the detectable level according to the kit instructions.

Test Example 5

DNA Profiles
(Step 1) Genomic DNA Isolation

Cells from three full-growth 75-cm$^2$ flasks were harvested using a cell scraper. After the cell pellets were washed three times with PBS, genomic DNA was prepared by the proteinase-K digestion and phenol-chloroform extraction method(Sambrook, J., et al., *Molecular Cloning: A Laboratory Manual*(2nd ed), Cold Spring Harbor Laboratory, New York(1989)).

(Step 2) Southern Hybridization for DNA Profiles

10 μg of each genomic DNA sample was digested with 70 units of HinfI restriction endonuclease, separated by 0.8% agarose gel electrophoresis, and then transferred to Hybond-N$^+$ nylon membrane(Amersham, Arlington Heights, Ill.). The membranes were pre-hybridized at 65° C. in 6×SSPE, 0.1% SDS, 5×Denhardt's solution, in the presence of sonicated salmon sperm DNA. Two polymorphic DNA probes, ChdTC-15 on chromosome 12 and ChdTC-114 on chromosome 20 were used for hybridization to detect variable numbers of tandem repeats (VNTRs). Hybridization to these highly polymorphic probes was performed as described in Honma, M. et al.("A New DNA-Profiling System for Cell-Line Identification for Use in Cell Banks in Japan", *In Vitro Cell Dev. Biol.*, 28A, 24–28(1991).

After hybridization, the membranes were washed twice for 20 minutes in 2×SSPE/0.1% SDS at room temperature, and twice for 10 minutes in 1×SSPE/0.1% SDS at 60° C. The hybridized membranes were exposed to Kodak XAR-5 film(Eastman Kodak, Rochester, N.Y.) for 1 to 3 days at −70° C.

As controls, the ovarian carcinoma cell line SK-OV-3 (Fogh, J., et al., "Absence of HeLa Cell Contamination in 169 Cell Lines Derived from Human Tumors", *J. Natl. Cancer Inst.*, 58, 209–214(1977)) and the cervical carcinoma cell line HeLa(Hay, R. J., et al., *Catalogue of Cell Lines and Hybridomas*(7th ed), American Type Culture Collection, Rockvilla, Md. (1992)) obtained from American Type Culture Collection(ATCC) were used.

Figure 4:
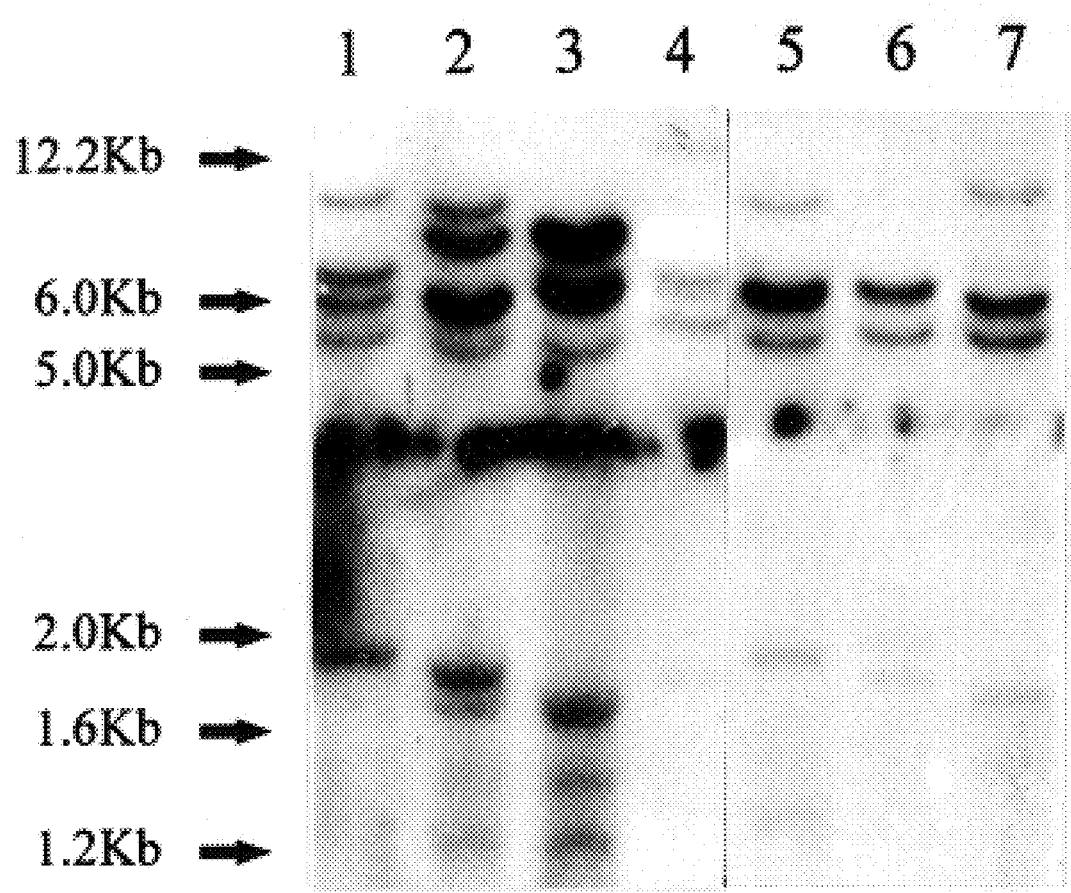
FIG. 4 discloses the DNA profiles of HinfI Southern blot of genomic DNAs from ovarian carcinoma cell lines, hybridized with ChdTC-15 and ChdTC-114.

FIG. 4 shows DNA profiles of HinfI Southern blot of genomic DNAs from ovarian carcinoma cell lines, hybridized with ChdTC-15 and ChdTC-114. In FIG. 4, lane 1 represents K-OV-3; lanes 2 to 6, SNU-8, SNU-119, SNU-251, SNU-563 and SNU-840, respectively; and lane 7, HeLa.

As can be seen in FIG. 4, the five SNU ovarian cell lines are unique, unrelated and diverse. Their DNA profiles are also different from those of two pre-existing ATCC cell lines, SK-OV-3 and HeLa. The number of allelic bands is more than 7 for ChdTC-114(1.2–5.1 Kb) and more than 10 for ChdTC-15(4.6–23.1 Kb). These results exclude possible cross-contamination between cell lines.

Test Example 6

Mutational Analysis of p53, BRCA1, hMLH1 and hMSH2 Genes

Polymerase chain reaction(PCR) and single-strand conformation polymorphism(SSCP) analysis were carried out as follows in order to screen the mutations in four ovarian cancer related tumor suppressor genes, p53, BRCA1, hMLH1 and hMSH2. All exons of these genes, except for those of p53, were screened. For the p53 gene, exon 4 to exon 9, in which about 98% of mutations in different cancers have been found(Nigro, S. J., et al., "Mutations in the p53 Gene Occur in Diverse Human Tumor Types", *Nature*, 342, 705–708(1989)), were screened.

The oligonucleotide primers used for amplification of the exons of these four genes have been previously described by Kang, M. S., et al.("Mutation of p53 Gene in Hepatocellular Carcinoma Cell Lines with HBX DNA", *Int. J. Cancer,* 67, 1–5(1996)), Miki, Y., et al.("A Strong Candidate for the Breast and Ovarian Cancer Susceptibility Gene BRCA1", *Science,* 266, 66–71(1994)), Han, H. J., et al.("Genomic Structure of Human Mismatch Repair Gene, hMLH1, and Its Mutation Analysis in Patients with Hereditary Nonpolyposis Colorectal Cancer (HNPCC)", *Hum. Mol. Genetics,* 2, 237–242(1995)) and Liu, B., et al. ("hMSH2 Mutations in Hereditary Nonpolyposis Colorectal Cancer Kindreds", *Cancer Res.,* 54, 4590–4594(1994)).

PCR-SSCP analysis was performed as described by Orita et al. ("Detection of Polymorphism of Human DNA by Gel Electrophoresis as Single Strand Conformation Polymorphism, *Proc. Natl. Acad. Sci. U.S.A.,* 86, 2766–2770(1989); and "A Rapid and Sensitive Detection of Point Mutations and Genetic Polymorphism Using Polymerase Chain Reaction", *Genomics,* 5, 874–879(1987)).

Each 10 ml of the reaction mixture contained 50–100 ng genomic DNA, 25 mM dNTPs, 0.5 U Taq polymerase, 25 nM of each sense and antisense primer, 10 mM Tris-HCl(pH 8.8), 50 mM KCl, 1.5 mM $MgCl_2$, 0.01% gelatin, and 0.2 ml [$\alpha$-$^{32}$P]dCTP (3000 Ci/mmol, Amersham Life Science, Little Chalfont, U. K.). Reaction mixtures were heated to 94° C. for 1.5 minutes, then cycled 35 times and finally elongated at 72° C. for 4 minutes. Each cycle consisted of denaturation at 94° C. for 30 seconds, annealing at 55–58° C. for 30 seconds, and strand elongation at 72° C. for 1 minute using a thermocycler(Perkin Elmer Cetus 9600, Roche Molecular Systems, Inc., New Jersey, U.S.A.).

After PCR, each reaction mixture was transferred into 10 ml of a loading buffer(95% formamide, 20 mM EDTA, 0.05% bromophenol blue, and 0.05% xylene cyanol FF). The samples were heated at 94° C. for 5 minutes and then quickly cooled on ice. 2 $\mu$l of each mixture was loaded onto a 3–5% polyacrylamide gel(acrylamide/bis-acrylamide, 19:1) in 0.5×TBE buffer(50 mM Tris-borate, 4 mM EDTA, pH 8.3). Electrophoresis was carried out with a sequencing gel apparatus(GIBCO/BRL) at 5 W for 12–18 hours in a cold room(16° C.).

After electrophoresis, gels were dried and subjected to autoradiography for 3 to 12 hours at room temperature.

Table 3 summarizes all mutations identified in this test.

amino acid change from proline to alanine. The other was a one-base "A" deletion at codon 132, which was a frameshift mutation that would lead to a stop codon 111 bp downstream and protein truncation. Cell line SNU-251 contained a 3-bp "TCA" deletion at codons 255 and 256 in exon 7. This was an in-frame deletion affecting two adjacent codons without shifting the open reading frame. Cell line SNU-563 exhibited a missense mutation from CGG to GGG at codon 282 in exon 8. The resulting change in amino acid was from arginine to glycine. In none of these three cell lines could the wild-type sequence of the p53 gene be detected, indicating the loss of both wild-type alleles.

All coding exons and intronic splice sites of the BRCA1 gene were screened for mutations using the PCR-SSCP method. Only one band of altered mobility was found on the SSCP film.

Test Example 7

DNA Sequencing Analysis

PCR products showing an aberrant migration pattern on the SSCP gels were directly cloned into a plasmid vector pCR II (Invitrogen Inc., San Diego, Calif., U.S.A.). Plasmid DNAs were extracted from multiple subclones or from more than 50 independent subclones for DNA sequencing templates. DNA sequences were determined by using the Automatic Sequencer(ABI Prism 377, Perkin Elmer, Foster City, Calif., U.S.A.).

Figure 5A:
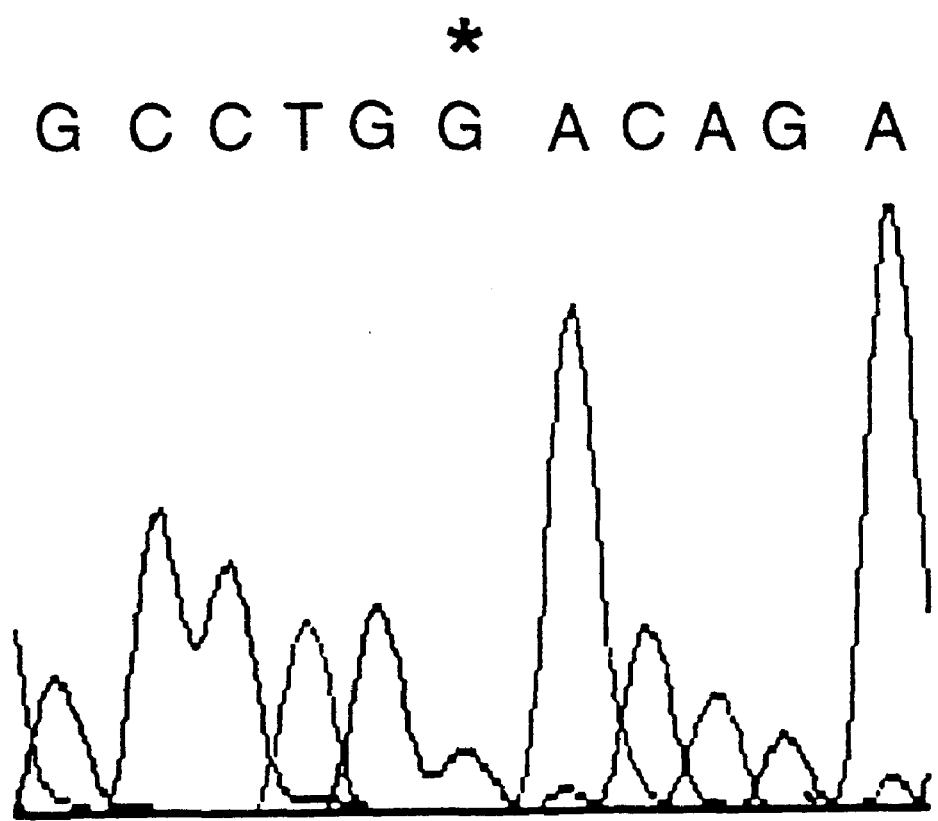
FIGS. 5A and 5B exhibit the sequencing analysis of the BRCA1 gene in normal (SEQ ID NO: 1) control and cell line SNU-251 (SEQ ID NO: 2), respectively.
Figure 5B:
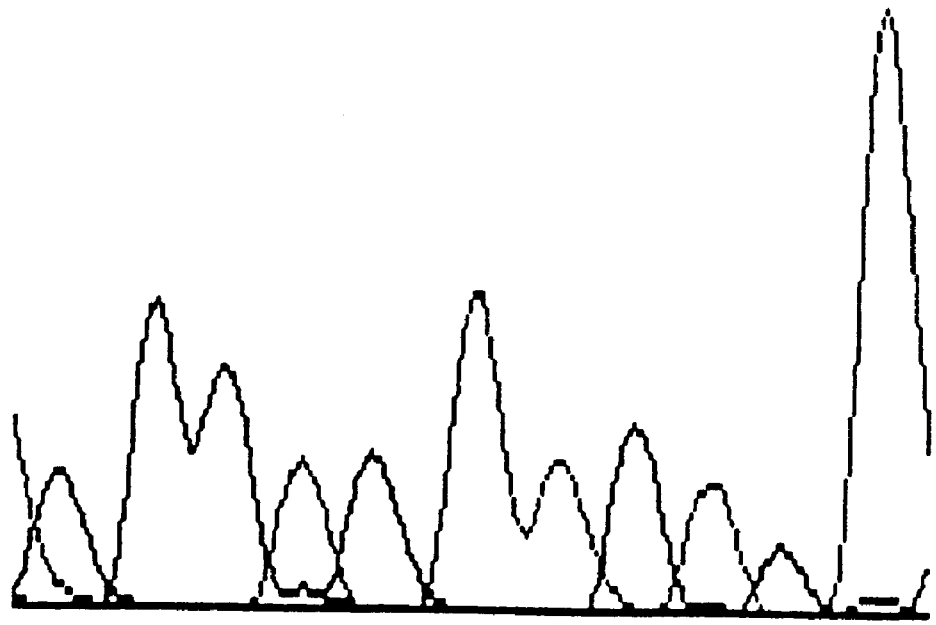

DNA sequencing analysis revealed that cell line SNU-251 has a nonsense mutation in exon 23. At codon 1815, TGG (Trp) was substituted with the stop codon TGA(FIGS. 5A and 5B), resulting in protein truncation. In FIGS. 5A and 5B, partial sequences from a normal control(FIG. 5A) and SNU-251(FIG. 5B) are shown and the base substitution from G to A at the third nucleotide of codon 1815 in exon 23 is indicated with asterisks. Also, no wild-type sequence of the BRCA1 gene could be detected in this cell line, indicating the loss of both wild-type copies of the gene.

In addition to mutations of the p53 and BRCA1 genes in cell line SNU-251, a heterozygous base substitution in the hMLH1 gene was also detected. This missense mutation from GCC to GAC at codon 723 of exon 19 leads to a change of alanine to aspartic acid at the amino acid level. None of the cell lines contained mutations of the hMSH2 gene.

TABLE 3

Mutations of Related Tumor Suppressor Genes in Ovarian Carcinoma Cell Lines

| Gene | Cell line | Exon | Codon | Mutation | Genotype |
|---|---|---|---|---|---|
| p53 | SNU-119 | 5 | 151 | Missense mutation, CCC(Pro) → GCC(Ala) | −[a]/− |
|  |  | 5 | 132 | Out-of-frame deletion, 1-bp, "A" deleted | −/− |
|  | SNU-251 | 7 | 255–256 | In-frame deletion, 3-bp, "TCA" deleted | −/− |
|  | SNU-563 | 8 | 282 | Missense mutation, CGG(Arg) → GGG(Gly) | −/− |
| BRCA1 | SNU-251 | 23 | 1815 | Nonsense mutation, TGG(Trp) → TGA(stop) | −/− |
| hMLH1 | SNU-251 | 19 | 723 | Missense mutation, GCC(Ala) → GAC(Asp) | +[b]/− |

[a]−: mutant-type
[b]+: wild-type

Four different mutations in the p53 gene were found in three of the five cell lines. Cell line SNU-119 displayed two different mutations in exon 5. One was a missense mutation from CCC to GCC at codon 151, which would lead to an It can be concluded that all the base substitutions found in the five cell lines are true mutations, rather than genetic polymorphisms which can be detected easily among the 50 normal controls.

While the invention has been described with respect to the above specific embodiments, it should be recognized that various modifications and changes may be made to the invention by those skilled in the art which also fall within the scope of the invention as defined by the appended claims.

What is claimed is:

1. A human ovarian carcinoma cell line designated SNU-251 (Deposit number: KCLRF-BP-00020) which has an in-frame 3-bp deletion at codons 255 and 256 in exon 7 of the p53 gene, a nonsense mutation of codon 1815 in exon 23 of the BRCA1 gene, and a missense mutation of codon 723 in exon 19 of the hMLH1 gene.

* * * * *

```
                          SEQUENCE LISTING (1) GENERAL INFORMATION:

(iii) NUMBER OF SEQUENCES: 2

(2) INFORMATION FOR SEQ ID NO: 1:

(i) SEQUENCE CHARACTERISTICS:
         (A) LENGTH: 11 base pairs
         (B) TYPE: nucleic acid
         (C) STRANDEDNESS: single
         (D) TOPOLOGY: linear (ii) MOLECULE TYPE: DNA (xi) SEQUENCE DESCRIPTION: SEQ ID NO: 1:

GCCTGGACAG A                                                            11

(2) INFORMATION FOR SEQ ID NO: 2:

(i) SEQUENCE CHARACTERISTICS:
         (A) LENGTH: 11 base pairs
         (B) TYPE: nucleic acid
         (C) STRANDEDNESS: single
         (D) TOPOLOGY: linear (ii) MOLECULE TYPE: DNA (xi) SEQUENCE DESCRIPTION: SEQ ID NO: 2:

GCCTGAACAG A                                                            11
```